(12) United States Patent
Heo

(10) Patent No.: US 12,562,278 B2
(45) Date of Patent: Feb. 24, 2026

(54) SERVICE PROVIDING SYSTEM CAPABLE OF PREDICTING AND DIAGNOSING STATE OF JOINTS, AND METHOD THEREFOR

(71) Applicant: AIFORPET, Pohang-si (KR)

(72) Inventor: Euna Heo, Seoul (KR)

(73) Assignee: AIFORPET, Pohang-si (KR)

( * ) Notice: Subject to any disclaimer, the term of this patent is extended or adjusted under 35 U.S.C. 154(b) by 39 days.

(21) Appl. No.: 18/282,214

(22) PCT Filed: Jan. 18, 2022

(86) PCT No.: PCT/KR2022/000869
§ 371 (c)(1),
(2) Date: Sep. 14, 2023

(87) PCT Pub. No.: WO2023/136388
PCT Pub. Date: Jul. 20, 2023

(65) Prior Publication Data
US 2024/0371519 A1     Nov. 7, 2024

(30) Foreign Application Priority Data

Jan. 7, 2022    (KR) ........................ 10-2022-0006399

(51) Int. Cl.
*G06K 9/00*        (2022.01)
*G06T 7/13*        (2017.01)
        (Continued)

(52) U.S. Cl.
CPC .............. *G16H 50/20* (2018.01); *G06T 7/13* (2017.01); *G06T 7/20* (2013.01); *G06V 10/25* (2022.01);
        (Continued)

(58) Field of Classification Search
CPC ........... G06K 9/00; G16H 50/20; A61K 35/12
        (Continued)

(56) References Cited

U.S. PATENT DOCUMENTS

2022/0215535 A1* 7/2022 Kong ........................ G06T 7/75
2022/0405933 A1* 12/2022 Tajbakhsh .............. G06N 3/096
        (Continued)

FOREIGN PATENT DOCUMENTS

KR    10-2003-0032088    4/2003
KR    10-2010-0052408    5/2010
        (Continued)

OTHER PUBLICATIONS

English Specification of 10-2003-0032088.
        (Continued)

*Primary Examiner* — Seyed H Azarian
(74) *Attorney, Agent, or Firm* — ZION IP; Byungwoong Park

(57)        ABSTRACT

Provided are a service providing system capable of predicting and diagnosing the state of joints, and a method therefor. The method relates to a service providing method capable of predicting and diagnosing the state of joints, which is performed by a server, the method comprising the steps of: extracting image information for each frame from photographed image data about a subject; extracting predictive joint data of the subject by inputting the image information for each frame to a pose estimation model in a plurality of convolutional layers of a convolutional neural network (CNN); and comparing and analyzing the predictive joint data extracted through the pose estimation model on the basis of standard data, and determining the presence of an abnormality in joints of the subject, to generate diagnosed result data, wherein the step of extracting the predictive joint data may comprise the steps of: recognizing the subject as an object by separating the subject from a background in the image information for each frame; setting a bounding box for each frame by detecting a boundary area around the object; extracting predictive coordinate information for each
        (Continued)

frame about a body part of the object located in the bounding box; extracting an object movement direction of the object located in the bounding box; and extracting the predictive joint data by labeling the predictive coordinate information on the basis of the object movement direction.

14 Claims, 16 Drawing Sheets

(51) Int. Cl.

| | | |
|---|---|---|
| *G06T 7/20* | (2017.01) | |
| *G06V 10/25* | (2022.01) | |
| *G16H 30/40* | (2018.01) | |
| *G16H 50/20* | (2018.01) | |

(52) U.S. Cl.
CPC ... *G16H 30/40* (2018.01); *G06T 2207/20044* (2013.01); *G06T 2207/20084* (2013.01); *G06V 2201/07* (2022.01)

(58) Field of Classification Search
USPC ....... 382/100, 103, 106, 110, 128, 132, 154, 382/157, 168, 173, 181, 199, 201, 219, 382/254, 276, 284–291, 305, 312; 600/408; 705/2
See application file for complete search history.

(56) References Cited

U.S. PATENT DOCUMENTS

| | | | | |
|---|---|---|---|---|
| 2023/0181257 A1* | 6/2023 | McGuan | ................ | G16H 10/60 |
| | | | | 705/2 |
| 2023/0190139 A1* | 6/2023 | Godbey | .............. | A61B 5/1121 |
| | | | | 600/408 |
| 2023/0248261 A1* | 8/2023 | Mun | ....................... | G06T 7/246 |
| | | | | 600/408 |
| 2024/0203567 A1* | 6/2024 | Ruiz | ..................... | G06T 7/0012 |
| 2025/0255672 A1* | 8/2025 | McKinnon | ........... | A61B 5/4585 |

FOREIGN PATENT DOCUMENTS

| | | |
|---|---|---|
| KR | 10-2018-0097949 | 9/2018 |
| KR | 10-2019-0036929 | 4/2019 |
| KR | 10-2020-0056674 | 5/2020 |
| KR | 10-2255483 | 5/2021 |

OTHER PUBLICATIONS

English Specification of 10-2255483.
English Specification of 10-2018-0097949.
English Specification of 10-2010-0052408.
English Specification of 10-2019-0036929.
English Specification of 10-2020-0056674.

* cited by examiner

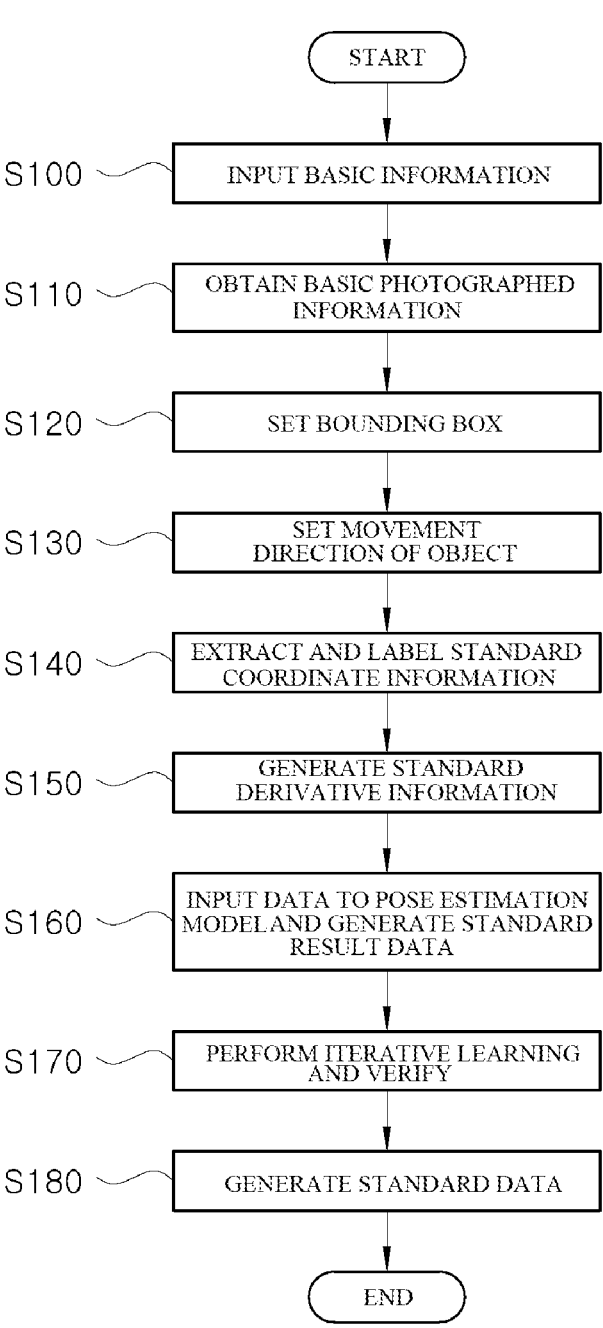

START

S100 — INPUT BASIC INFORMATION

S110 — OBTAIN BASIC PHOTOGRAPHED INFORMATION

S120 — SET BOUNDING BOX

S130 — SET MOVEMENT DIRECTION OF OBJECT

S140 — EXTRACT AND LABEL STANDARD COORDINATE INFORMATION

S150 — GENERATE STANDARD DERIVATIVE INFORMATION

S160 — INPUT DATA TO POSE ESTIMATION MODEL AND GENERATE STANDARD RESULT DATA

S170 — PERFORM ITERATIVE LEARNING AND VERIFY

S180 — GENERATE STANDARD DATA

END

FIG. 5
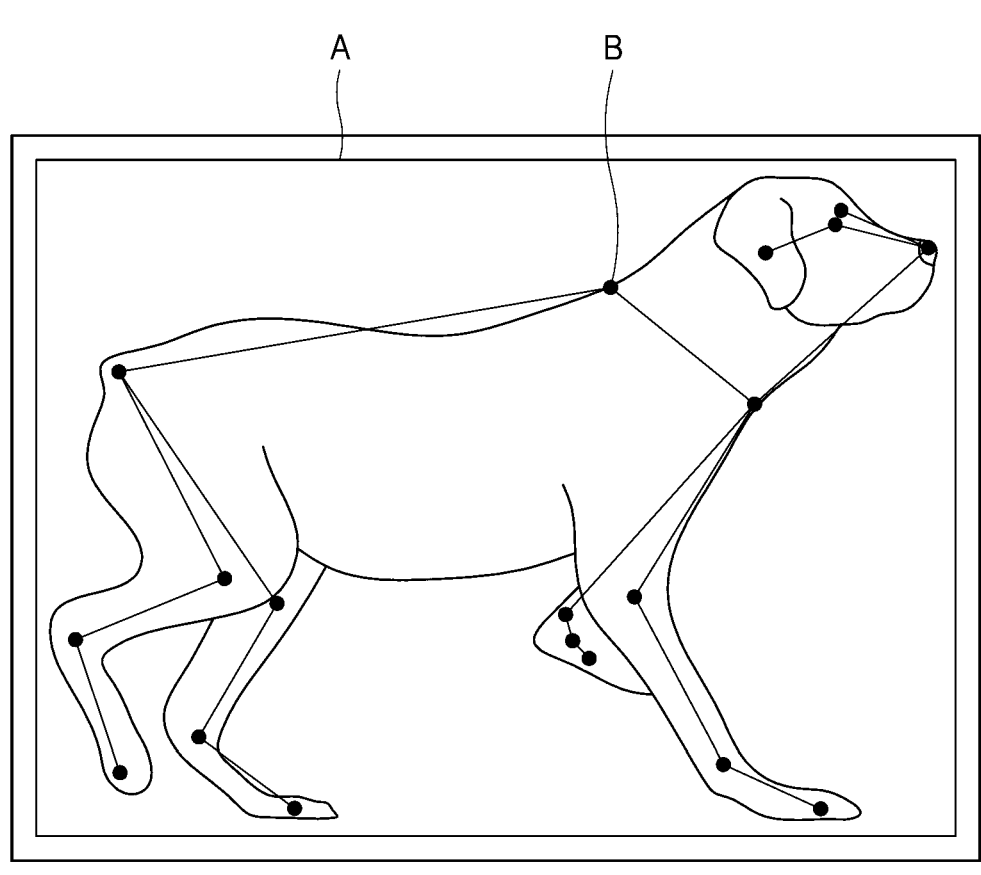

FIG. 6

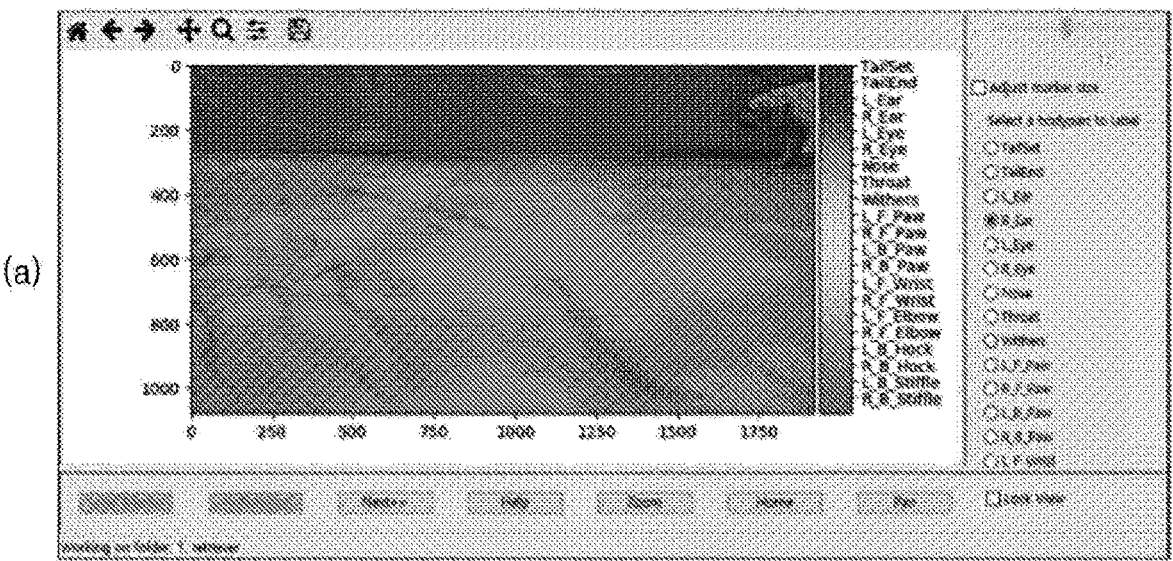

(a)

(b)

| scorer | teamDLC | teamDLC | teamDLC | teamDLC |
|---|---|---|---|---|
| bodyparts | Nose | Nose | L_Eye | L_Eye |
| coords | x | y | x | y |
| labeled-data\210728_pose_side\pose_side_001.png | 102.3037007 | 86.59285276 | 122.3202348 | 73.98482938 |
| labeled-data\210728_pose_side\pose_side_002.png | 140.5485203 | 56.60479905 | 152.2257639 | 55.40297417 |
| labeled-data\210728_pose_side\pose_side_006.png | 240.633796 | 38.60253502 | | |
| labeled-data\210728_pose_side\pose_side_007.png | 89.62260392 | 69.57406967 | 104.4116359 | 54.26612034 |
| labeled-data\210728_pose_side\pose_side_008.png | 96.5255463 | 60.32998035 | 110.64302 | 51.60281481 |
| labeled-data\210728_pose_side\pose_side_009.png | 95.98989939 | 32.52075853 | 112.5239742 | 26.35132762 |
| labeled-data\210728_pose_side\pose_side_010.png | 186.9169074 | 59.11065306 | | |
| labeled-data\210728_pose_side\pose_side_011.png | 160.1948265 | 72.16863268 | 159.1569997 | 56.86068735 |
| labeled-data\210728_pose_side\pose_side_012.png | 25.66606008 | 108.9529575 | 38.75248965 | 99.96980094 |

...

(c)

CollectedData_sl.csv   CollectedData_sl.05   img0146.png   img0193.png img1004.png   img1173.png   img1183.png   img1278.png img1852.png   img1707.png   img1737.png   img1773.png FIG. 12
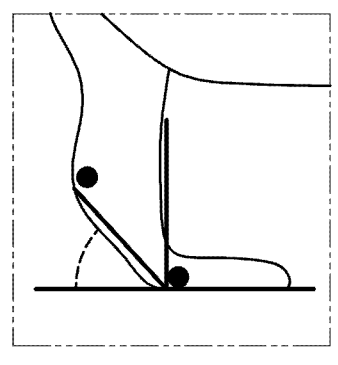 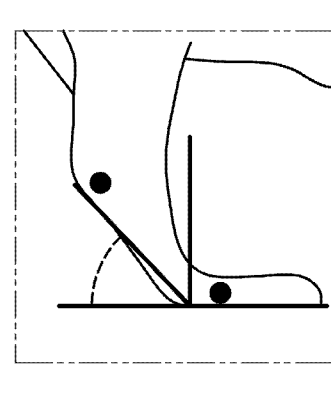 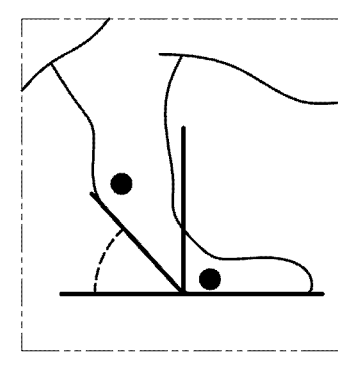
(a)
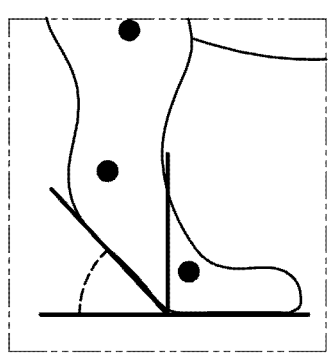 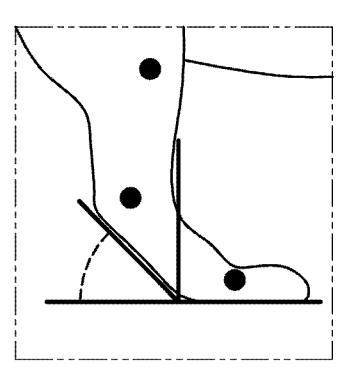 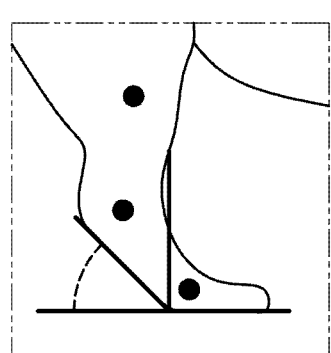
(b)

FIG. 13
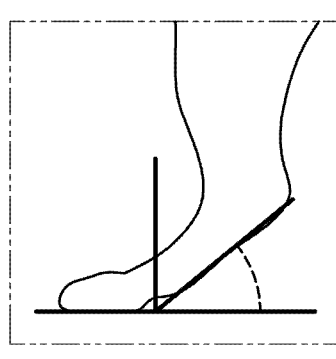 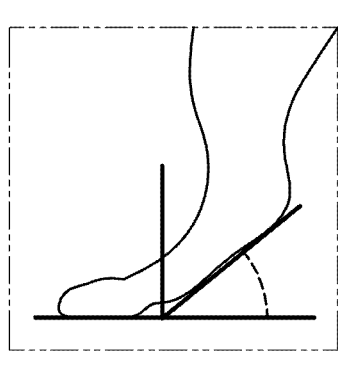 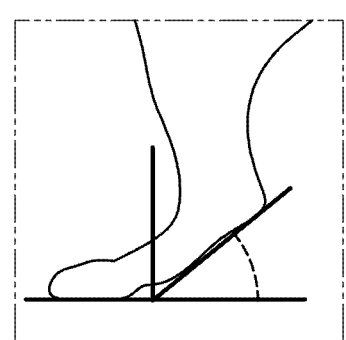
(a)
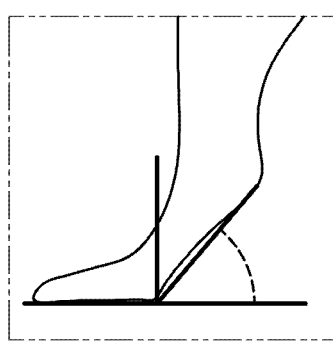 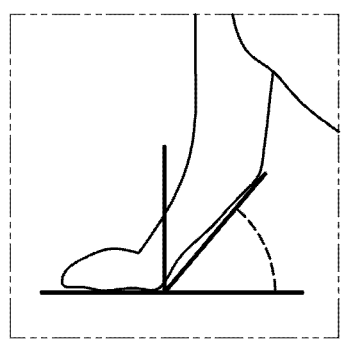 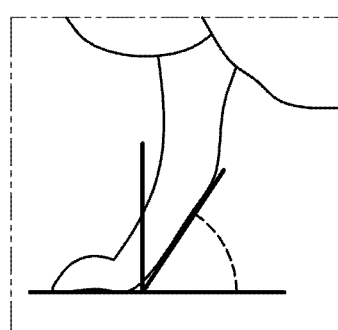
(b)

SERVICE PROVIDING SYSTEM CAPABLE OF PREDICTING AND DIAGNOSING STATE OF JOINTS, AND METHOD THEREFOR

TECHNICAL FIELD

The present invention relates to a service providing system for predicting and diagnosing a joint condition and a method thereof, and more specifically, to a service providing system for predicting and diagnosing a joint condition that can predict luxation of a patella and hip joint of an animal and determine whether there is an abnormality in a non-face-to-face manner using a video obtained from a user, and a method thereof.

Background Art

Recently, as population aging has progressed in the population structure and single households have increased, human beings have been gradually becoming self-centered and desolate. Accordingly, the number of people who recognize companion animals as family members or companions is increasing, and the companion animal market is also growing steadily.

When abnormal symptoms occur in companion animals, most people have taken their companion animals to veterinary hospitals for treatment, or have resolved abnormal symptoms that have occurred in their companion animals on the basis of information obtained from nearby people or obtained through the Internet, phones, etc.

For example, patellar luxation, which is a common condition in aging dogs, is a disease in which a patella above a knee joint is out of alignment, and is caused by trauma, a congenital defective shape of the joint, or when a previously healthy knee joint develops abnormalities with age.

Patellar luxation is known to occur especially in certain small dogs such as toy poodles, Pomeranians, Yorkshire terriers, Maltese dogs, and the like. In severe cases, the misaligned joints swell or the ligaments rupture, causing severe pain, and thus companion dogs show the appearance of dragging their legs or walking with their legs raised. In the case of entities that are vulnerable to or have a high probability of developing patellar luxation, the onset of the disease can be delayed by intensive management in advance. That is, it is possible to prevent patellar luxation through training to avoid actions that put too much strain on the joint, physical therapy, feed that is good for joints, maintaining an appropriate weight, making an appropriate living environment to avoid trauma, exercise, massage, and the like, and it is possible to perform corrective surgery in advance at an early stage. Therefore, in order to prevent patellar luxation and improve the quality of life of companion dogs, a method that enables early prediction and diagnosis of patellar luxation is required.

However, there is much incorrect information obtained from nearby people or obtained through the Internet, phones, etc., and thus the disease may be difficult to treat, and even when visiting the hospital directly, there are many cases where the waiting time at the hospital is long and the service is not properly provided to the customer due to the heavy hospital workload.

The content described as the related art above is only for improving understanding of the related art of the present invention, and should not be taken as an admission that the content corresponds to related art already known to those skilled in the art.

RELATED ART DOCUMENT

Patent Document (Patent Document 1) Korean Laid-open Patent Application No. 2003-0032088 (published on Apr. 26, 2003)

Disclosure

Technical Problem

The present invention is directed to providing a service providing system for predicting and diagnosing a joint condition and a method thereof.

Objects of the present invention are not limited to the above-described object and other objects that are not described may be clearly understood by those skilled in the art from the following descriptions.

Technical Solution

One aspect of the present invention provides a service providing method for predicting and diagnosing a joint condition, which is performed by a server, which includes extracting frame-by-frame image information from photographed image data of a subject; inputting the frame-by-frame image information to a pose estimation model among a plurality of convolution layers of a convolution neural network (CNN) and extracting predicted joint data of the subject; and comparing and analyzing the predicted joint data extracted through the pose estimation model on the basis of standard data, determining whether there is an abnormality in a joint of the subject, and generating diagnosis result data, wherein the extracting of the predicted joint data includes separating the subject and a background from the frame-by-frame image information and recognizing the subject as an object, detecting a boundary area around the object and setting a bounding box for each frame, extracting frame-by-frame predicted coordinate information about a body part of the object located in the bounding box, and labeling the predicted coordinate information on the basis of the object movement direction and extracting the predicted joint data.

The extracting of the predicted joint data may include generating a derived variable using the predicted coordinate information, and inputting the derived variable to the pose estimation model on the basis of the standard data and extracting the predicted joint data.

In the generating of the result data, the predicted coordinate information and standard coordinate information may be matched for each frame on the basis of the standard data, and when a result of the matching is greater than or equal to a preset criterion, result data indicating that it is determined that there is an abnormality in the joint of the subject may be generated.

The derived variable may include at least one of a step height between right and left paws of the object, a number of frames corresponding to a change in movement of the object, at least one leg angle of the object, and movements of a neck and tail of the object.

In the generating of the result data, a difference in step height between the right and left paws of the object may be analyzed, and when the difference in step height is greater than or equal to a set average value on the basis of the standard data, result data indicating that it is determined that there is an abnormality in the joint of the subject may be generated.

In the generating of the result data, a difference in number of frames corresponding to a change in movement of the object may be analyzed, and when the difference in number of frames is greater than or equal to a set average value on the basis of the standard data, result data indicating that it is determined that there is an abnormality in the joint of the subject may be generated.

In the generating of the result data, at least one leg angle of the object may be analyzed and a difference in leg angle corresponding to a change in movement may be analyzed, and when the difference in leg angle is greater than or equal to a set average value on the basis of the standard data, result data indicating that it is determined that there is an abnormality in the joint of the subject may be generated.

In the generating of the result data, the movements of the neck and tail of the object may be analyzed and a difference in coordinate values corresponding to a change in movement may be analyzed, and when a mean squared error (MSE) is greater than or equal to a set average value on the basis of the standard data, result data indicating that it is determined that there is an abnormality in the joint of the subject may be generated.

The method may further include generating the standard data, wherein the generating of the standard data may include extracting an image for each frame from a video, extracting and labeling standard coordinate information about a body part of an object included in the extracted image, generating a standard derived variable using the standard coordinate information, setting a standard parameter on the basis of the standard derived variable and then inputting the set standard parameter to the pose estimation model, and iteratively learning standard joint data obtained through the pose estimation model and standard result data corresponding to the standard joint data and verifying the generated standard data.

The method may further include labeling the predicted joint data for each frame that is extracted through the pose estimation model for each subject.

The photographed image data may be a video file in which the subject walking in a consistent direction is recorded for 10 seconds or longer.

Another aspect of the present invention provides a service providing system for predicting and diagnosing a joint condition, which includes a user terminal configured to obtain photographed image data from a subject to be examined; and a management server configured to extract frame-by-frame image information from the photographed image data of the subject, input the frame-by-frame image information to a pose estimation model among a plurality of convolution layers of a CNN to extract predicted joint data of the subject, compare and analyze the predicted joint data extracted through the pose estimation model on the basis of standard data, determine whether there is an abnormality in a joint of the subject, and generate diagnosis result data, wherein the management server separates the subject and a background from the frame-by-frame image information to recognize the subject as an object, detects a boundary area around the object to set a bounding box for each frame, extracts frame-by-frame predicted coordinate information about a body part of the object located in the bounding box, extracts an object movement direction of the object located in the bounding box, and labels the predicted coordinate information on the basis of the object movement direction to extract the predicted joint data.

The system may further include a service-linked terminal configured to share medical treatment management data generated in response to the result data.

The system may further include a manager terminal configured to learn the standard data and generate the result data corresponding to the photographed image data.

Still another aspect of the present invention provides a program which is stored in a computer-readable recording medium to perform the service providing method for predicting and diagnosing the joint condition in combination with a computer that is hardware.

Other specific details of the present invention are included in detailed descriptions and the accompanying drawings.

Advantageous Effects

According to the present invention, it is possible to predict luxation of a patella of an animal and determine whether there is an abnormality in a non-face-to-face manner using a video obtained from a user, thereby increasing convenience and reliability while respecting the diversity of users.

According to the present invention, when there is an abnormality in a joint of a test subject, in particular, a companion animal, a current condition of the companion animal can be rapidly and accurately determined using a portable terminal, thereby giving a guardian of the companion animal confidence.

According to the present invention, by accurately diagnosing a current condition of a companion animal in real time using a portable terminal, user convenience and reliability can be enhanced.

According to the present invention, by receiving hospital information about a current condition of a companion animal, it is possible to treat a disease of the companion animal at a hospital capable of responding to the disease of the companion animal to preserve the health of the companion animal.

According to the present invention, by continuously providing notification information about a companion animal to a guardian, it is possible to guide revisiting of a veterinary hospital and prevent withdrawal.

According to the present invention, by sharing examination results of companion animals, it is possible to more accurately check a condition of the companion animal and respond to it, thereby giving a guardian of the companion animal confidence.

Effects of the present invention are not limited to the above-described effects and other effects that are not described may be clearly understood by those skilled in the art from the following descriptions.

DESCRIPTION OF DRAWINGS

FIG. 4 is a diagram for describing an operation of generating standard data illustrated in FIG. 3.

FIG. 5 is a diagram for describing basic photographed information illustrated in FIG. 4.

FIG. 6 is a set of diagrams for describing an operation of extracting and labeling standard coordinate information illustrated in FIG. 4.

FIG. 12 is a set of diagrams for describing a normal leg angle illustrated in FIG. 7.

FIG. 13 is a set of diagrams for describing an abnormal leg angle illustrated in FIG. 7.

MODES OF THE INVENTION

Figure 1:
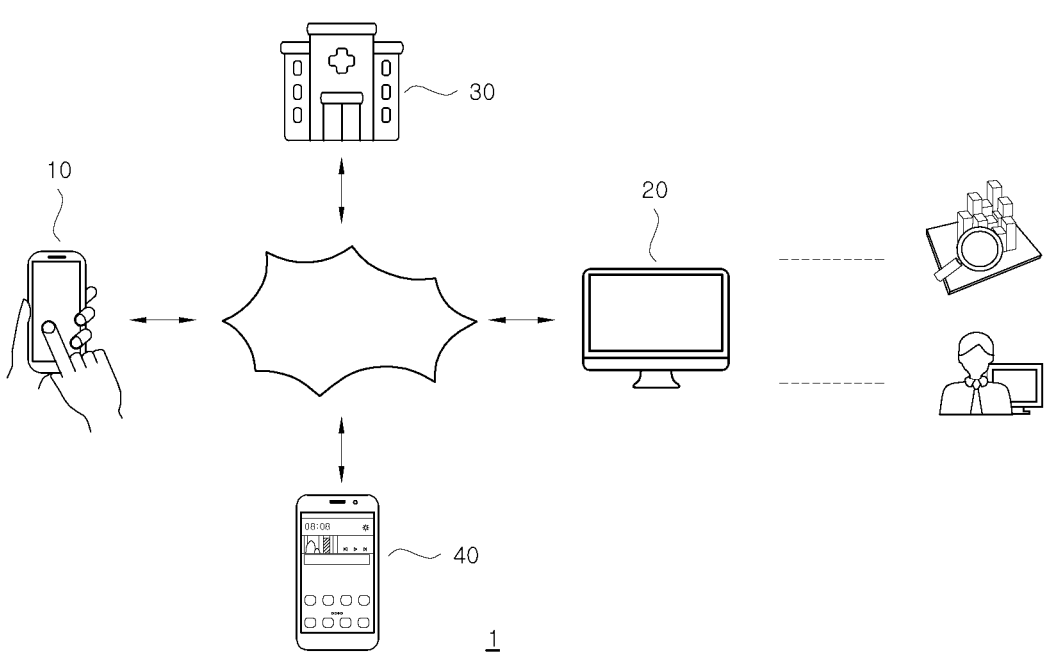
FIG. 1 is a conceptual diagram for describing a service providing system for predicting and diagnosing a joint condition according to an embodiment of the present invention.

Advantages and features of the present invention and methods of achieving the same will be clearly understood with reference to the accompanying drawings and embodiments described in detail below. However, the present invention is not limited to the embodiments to be disclosed below but may be implemented in various different forms. The embodiments are provided in order to fully explain the present embodiments and fully explain the scope of the present invention for those skilled in the art. The scope of the present invention is only defined by the appended claims.

Terms used in the embodiments of the present invention are provided only to describe embodiments of the present invention and not for purposes of limitation. In this specification, the singular forms include the plural forms unless the context clearly indicates otherwise. It will be understood that the terms "comprise" and/or "comprising," when used herein, do not preclude the presence or addition of one or more components other than the described components. Like reference numerals refer to like components throughout the specification, and the term "and/or" includes any and all combinations of the described components. It should be understood that, although the terms "first," "second," etc. may be used herein to describe various components, these components are not limited by these terms. The terms are only used to distinguish one component from another component. Therefore, it should be understood that a first component to be described below may be a second component within the technical scope of the present invention.

Unless otherwise defined, all terms (including technical and scientific terms) used herein can be used as is customary in the art to which the present invention pertains. In addition, it will be further understood that terms, such as those defined in commonly used dictionaries, will not be interpreted in an idealized or overly formal sense unless expressly so defined herein.

Hereinafter, embodiments of the present invention will be described in detail with reference to the accompanying drawings.

Figure 2:
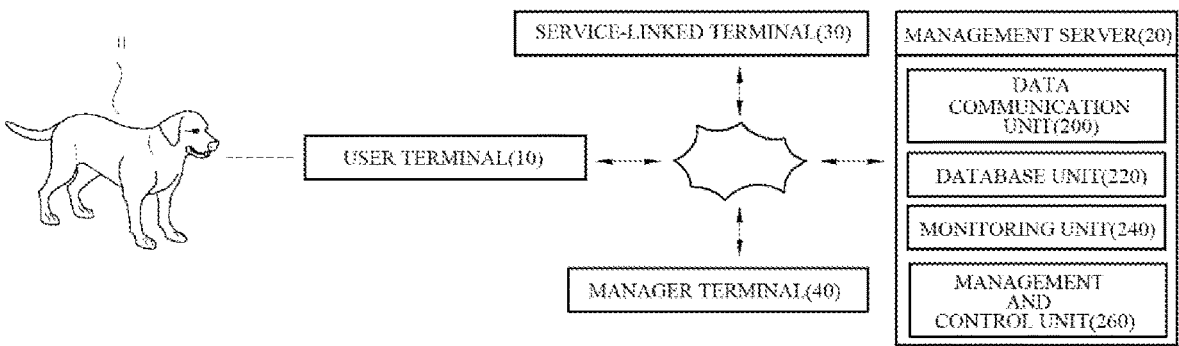
FIG. 2 is a diagram for describing a detailed configuration of the service providing system for predicting and diagnosing the joint condition illustrated in FIG. 1.

FIG. 1 is a conceptual diagram for describing a service providing system for predicting and diagnosing a joint condition according to an embodiment of the present invention, and FIG. 2 is a diagram for describing a detailed configuration of the service providing system for predicting and diagnosing the joint condition illustrated in FIG. 1.

As illustrated in FIGS. 1 and 2, a service providing system 1 for predicting and diagnosing a joint condition, which is an embodiment of the present invention, may include a user terminal 10, a management server 20, a service-linked terminal 30, and a manager terminal 40. In this case, the manager terminal 40 may be omitted.

Here, the user terminal 10, the management server 20, the service-linked terminal 30, and the manager terminal 40 may be synchronized in real time using a wireless communication network to transmit or receive data to or from each other. Various remote communication methods may be supported by the wireless communication network, and various communication methods such as a wireless local area network (WLAN), Digital Living Network Alliance (DLNA), wireless broadband (Wibro), Worldwide Interoperability for Microwave Access (Wimax), Global System for Mobile Communications (GSM), code-division multi access (CDMA), code-division multi access 2000 (CDMA2000), enhanced voice-data optimized or enhanced voice-data only (EV-DO), wideband CDMA (WCDMA), high speed downlink packet access (HSDPA), high speed uplink packet access (HSUPA), Institute of Electrical and Electronics Engineers (IEEE) 802.16, Long-Term Evolution (LTE), LTE Advanced (LTEA), a wireless mobile broadband service (WMBS), Bluetooth Low Energy (BLE), Zigbee, radio frequency (RF), long range (LoRa), and the like may be applied, but the present invention is not limited thereto, and various widely known wireless or mobile communication methods may be applied.

First, in the present embodiment, although it has been disclosed that a subject is limited to, for example, a companion animal, in particular, a puppy, the companion animal's gait is photographed, and whether there is an abnormality in a joint is determined using the service providing system 1 for predicting and diagnosing the joint condition, the present invention is not limited thereto. For example, it is possible to determine whether there is an abnormality by predicting and measuring not only joint-related diseases of various animals, including vertebrates such as mammals, birds, reptiles, amphibians, fish, etc., and invertebrates such as arthropods and mollusks, which are living with guardians, companions, or dog owners (hereinafter referred to as guardians), but also joint conditions of humans.

The user terminal 10 is a portable terminal possessed by a guardian of a companion animal 11, and may operate using an application program (or application) in the present disclosure, and such an application program may be downloaded from an external server or the management server 20 through wireless communication. For example, the user terminal 10 may include various terminals such as smartphones, personal digital assistants (PDAs), tablet computers, wearable devices (e.g., watch type terminals (smartwatches), glasses type terminal (smart glasses), head mounted displays (HMDs), etc.), and various types of Internet of Things (IOT) terminals, but the present invention is not limited thereto.

The user terminal 10 may recognize a non-jumping movement of the companion animal 11 to obtain photographed image data obtained by mainly photographing a gait pattern.

For example, the photographed image data may be a video file in which the companion animal 11, which is a subject for which a joint condition is predicted and diagnosed, walking in a consistent direction is recorded for 10 seconds or longer.

That is, the user terminal 10 may photograph movements of the companion animal 11 moving from left to right from the front, side, or rear in the same direction.

Here, the photographed image data may include information about a photograph and/or video in a state in which the companion animal 11 needs to be managed. For example, the photographed image data may include a video obtained by photographing the movements of the companion animal 11, but the present invention is not limited thereto.

In some embodiments, the user terminal 10 may automatically adjust brightness, sharpness, and the like of the photographed image data in consideration of a surrounding environment, shaking, a movement speed, hair color, and the like. Further, the user terminal 10 may receive and output result data corresponding to the photographed image data.

In this case, the result data may be data including a result of determining whether there is an abnormality in the joint of the companion animal 11 using the photographed image data on the basis of standard data.

Further, the standard data may be data generated by matching standard condition information of the companion animal 11 and standard result data. The standard condition information may include basic information, basic photographed information, and standard coordinate information. The basic information may include guardian information, abandonment information, hospital record information, unique identification number, dog breed or cat breed, sex, age, weight, neutered status, etc., the guardian information may include contact information, etc., and the hospital record information may include vaccination information, medical treatment information, the presence or absence of allergies, etc. In this case, in some embodiments, the hospital record information may include beauty information. The basic photographed information may include video information, and the standard coordinate information may be coordinate information displayed on a body part of the companion animal 11 that can determine whether there is an abnormality in the joint in response to the video information.

The standard result data may be data obtained by determining whether there is an abnormality in the joint using the basic photographed information.

In some embodiments, the standard result data may include progress stages for each disease regarding the presence or absence of joint abnormalities, and the like. In this case, the standard result data may be visually determined, but the present invention is not limited thereto.

Further, the user terminal 10 may transmit or receive medical treatment management data. Here, the medical treatment management data may include recommendation information that can be recommended according to a current condition or disease condition of the companion animal 11, reservation management information, veterinary hospital connection information, and hospital record information, but the present invention is not limited thereto.

For example, when the user terminal 10 outputs the medical treatment management data, the user terminal 10 may display hospital information such as a location, contact information, and reservation available dates of a hospital corresponding to the recommendation information generated on the basis of the veterinary hospital connection information together with a road view, a map, or a calendar, display the hospital record information including treatment history information, prevention information, etc., or display the reservation management information including a reservation completion signal received in response to a reservation request signal of the user terminal 10 on a screen.

Further, the user terminal 10 is a device for visually and audibly displaying a current operating state of the user terminal 10, and may include a display that can output symbols, characters, numbers, etc. on a screen according to the operating state, a lamp that outputs color changes or flickering, a speaker that outputs audio, or the like.

For example, when result data is output after the measurement of the companion animal 11 is completed, a display unit may display the result data in O/X, blink a screen in red or green, display a guide phrase such as "No issue" or "A visit to the hospital is recommended," or display dictionary information about the result data.

Further, the user terminal 10 may store a plurality of application programs (or applications) to be executed in the user terminal 10, data for operation of the user terminal 10, and commands. At least some of the application programs may be downloaded from an external server through wireless communication.

In other words, the user terminal 10 may predict and diagnose the condition of the joint of the companion animal 11 in a non-face-to-face manner regardless of time and place using a portable terminal. Accordingly, it is possible to check the health condition of the companion animal 11 and treat the disease at an early stage to preserve the health of the companion animal 11, thereby increasing convenience and reliability while respecting the diversity of guardians.

The management server 20 may include a data communication unit 200, a database unit 220, a monitoring unit 240, and a management and control unit 260.

When the photographed image data is received from the user terminal 10, the data communication unit 200 may transmit the result data to the user terminal 10.

In some embodiments, when the standard data is transmitted to the user terminal 10, the data communication unit 200 may receive the result data from the user terminal 10.

Further, the data communication unit 200 may allow the medical treatment management data to be transmitted or received between the user terminal 10 and the management server 20.

In some embodiments, the data communication unit 200 may allow the medical treatment management data to be transmitted or received between the user terminal 10 and the service-linked terminal 30.

The database unit 220 may store data transmitted or received between the user terminal 10 and the service-linked terminal 30 through a wireless communication network. In this case, the standard data may be updated and stored in real time in response to the result data.

The database unit 220 may store data for supporting various functions of the management server 20. The database unit 220 may store a plurality of application programs (or applications) to be executed in the management server 20, data for operation of the management server 20, and commands. At least some of the application programs may be downloaded from an external server through wireless communication.

Meanwhile, the standard condition information, the photographed image data, the result data, and the standard data that are stored in the database unit 220 and used in the present embodiment may be implemented in the form of mapping tables that correspond to each other, but the present invention is not limited thereto.

The monitoring unit 240 may monitor an operating state of the user terminal 10, an operating state of the management server 20, data transmitted or received between the user terminal 10 and the management server 20, and the like through a screen. That is, by checking the usage state of the user terminal 10 in real time, it is possible to give the guardian more confidence by making usage convenient for the guardian.

When the photographed image data is received from the user terminal 10, the management and control unit 260 may generate the result data on the basis of the standard data.

Specifically, the management and control unit 260 may pre-process the video included in the photographed image data, extract frame-by-frame image information from the video, then extract predicted joint data by inputting the frame-by-frame image information to a pose estimation model among a plurality of convolution layers of a convolutional neural network (CNN), compare and analyze the predicted joint data to determine whether there is an abnormality in the joint, and generate diagnosis result data.

For example, when the photographed image data is information obtained by photographing the movement to check the joint condition of the companion animal 11, the management and control unit 260 may extract the frame-by-frame image information for joint analysis from the video in which brightness, sharpness, etc. are automatically corrected, included in the photographed image data. The companion animal 11 may be recognized as an object by separating the companion animal 11 and the background from the frame-by-frame image information. A bounding box is set for each frame by detecting a boundary area around the recognized object, frame-by-frame predicted coordinate information about the body part of the object located in the set bounding box is extracted, and then the predicted joint data may be extracted by labeling the predicted coordinate information on the basis of an object movement direction of the object. In this case, it is preferable that the object movement direction of the object located in the bounding box move in one direction.

In the present embodiment, examples of the body part may include a body part of the companion animal 11, such as a leg, a neck, a tail, etc., but the present invention is not limited thereto.

Further, the management and control unit 260 may generate a derived variable using the extracted predicted coordinate information, and extract the predicted joint data by inputting the generated derived variable to the pose estimation model. In this case, the extracted predicted joint data may be labeled for each frame on the basis of the standard data.

Specifically, the management and control unit 260 may generate the derived variable for at least one variable among a step height between right and left paws of the object, a number of frames corresponding to a change in movement of the object, at least one leg angle of the object, and movements of a neck and tail of the object to generate the predicted joint data using the generated derived variable, and then analyze the predicted joint data corresponding to the photographed image data on the basis of the standard data to generate the result data.

For example, the management and control unit 260 may analyze a difference in step height between the right and left paws of the object, and when the difference in step height is greater than or equal to a set average value on the basis of the standard data, the management and control unit 260 may generate the result data indicating that it is determined that there is an abnormality in the joint of the companion animal 11.

Further, the management and control unit 260 may analyze a difference in number of frames corresponding to the change in movement of the object, and when the difference in number of frames is greater than or equal to a set average value on the basis of the standard data, the management and control unit 260 may generate the result data indicating that it is determined that there is an abnormality in the joint of the companion animal 11.

Further, the management and control unit 260 may analyze at least one leg angle of the object and analyze a difference in leg angle corresponding to the change in movement, and when the difference in leg angle is greater than or equal to a set average value on the basis of the standard data, the management and control unit 260 may generate the result data indicating that it is determined that there is an abnormality in the joint of the companion animal 11.

Further, the management and control unit 260 may analyze movements of the neck and tail of the object and analyze a difference in coordinate values corresponding to the change in movement, and when a mean squared error (MSE) is higher than or equal to a set average value on the basis of the standard data, the management and control unit 260 may generate the result data indicating that it is determined that there is an abnormality in the joint of the companion animal 11. In this case, the MSE may represent an average error square value of y-coordinate values (height) of the neck or tail of the companion animal 11 with a joint abnormality and the companion animal 11 without a joint abnormality, among companion animals 11 of similar size.

In some embodiments, the management and control unit 260 may match the predicted coordinate information and the standard coordinate information for each frame on the basis of the standard data, and when a result of the matching is greater than or equal to a preset criterion, the management and control unit 260 may generate the result data indicating that it is determined that there is an abnormality in the joint of the companion animal 11.

In some embodiments, the management and control unit 260 may generate derived variables for a step height between the right and left paws of the object, a number of frames corresponding to the change in movement of the object, at least one leg angle of the object, and movements of the neck and tail of the object to generate the predicted joint data using the generated derived variable, and generate the result data corresponding to the photographed image data on the basis of the standard data.

Meanwhile, the management and control unit 260 may filter the photographed image data. In this case, in the filtering, the image may be obtained by filtering the degree of shaking of the image using a Laplace filter, but the present invention is not limited thereto.

In some embodiments, when the standard data is transmitted to the user terminal 10, the management and control unit 260 may receive the result data corresponding to the photographed image data of the companion animal 11.

Further, the management and control unit 260 may generate the standard data by matching the standard condition information and the standard result data using deep learning. Although described as using deep learning in this embodiment, the present invention is not limited thereto, and machine learning techniques such as random forest, support vector machine, or the like may be used. In this case, the management and control unit 260 may update the standard data in real time in response to the result data.

Specifically, the management and control unit 260 may generate the standard data by repeatedly learning the standard condition information and the standard result data based on a CNN algorithm and verifying suitability.

For example, the management and control unit 260 may obtain basic information from a plurality of companion animals 11 and analyze the obtained basic information to generate the standard result data. In this case, the basic information may be information obtained from dogs in facilities such as abandoned dog centers, shelters, etc., but the present invention not limited thereto, and the basic information may also be information obtained from cats in abandoned cat center facilities.

Further, the management and control unit 260 may manage the medical treatment management data transmitted and received between the user terminal 10 and the service-linked terminal 30 on the basis of the result data. Here, the medical treatment management data may include recommendation information that can be recommended according to a current condition or disease condition of the companion animal 11, reservation management information, veterinary hospital connection information, and hospital record information.

For example, according to the result data, when treatment is required, the management and control unit 260 may provide recommendation information generated based on hospital information to the user terminal 10. In this case, the recommendation information may be information for recommending hospital information corresponding to the result data using veterinary hospital connection information generated based on the hospital information provided from the service-linked terminal 30.

Further, the management and control unit 260 may transmit or receive reservation management information to or from the user terminal 10 and the service-linked terminal 30.

For example, the management and control unit 260 may transmit a reservation request signal received from the user terminal 10 to the service-linked terminal 30, and transmit a reservation completion signal generated in response to the reservation request signal from the service-linked terminal 30 to the user terminal 10.

Further, the management and control unit 260 may transmit hospital record information to the user terminal 10. In this case, the management and control unit 260 may receive the hospital record information from the service-linked terminal 30.

For example, when the treatment of the companion animal 11 is completed, the management and control unit 260 may transmit hospital record information including treatment history information to the user terminal 10, and in general, the management and control unit 260 may transmit hospital record information including prevention information or beauty information to the user terminal 10. Further, the management and control unit 260 may transmit notification information about the companion animal 11 to the user terminal 10. In this case, the notification information is information generated by the service-linked terminal 30 and may be notification information about treatment or grooming of the companion animal 11, but the present invention is not limited thereto.

In some embodiments, the management and control unit 260 may share the hospital record information with other servers.

In some embodiments, the management and control unit 260 may insert and transmit or receive advertisement information together with the data transmitted to or received from the user terminal 10, the service-linked terminal 30, and/or the manager terminal 40. Accordingly, additional advertising revenue may be generated to support facilities such as abandoned dog centers, abandoned cat centers, shelters, and the like.

The management server 20 having such a structure may automatically extract a diagnosis part from the photographed image data obtained through the user terminal 10 on the basis of the standard data verified by repeatedly learning the standard result data labeled in response to the standard condition information obtained from the plurality of companion animals 11, compare and analyze extracted images to analyze a plurality of diseases, and generate result data obtained by determining whether there is an abnormality in the joint. Accordingly, it is possible to solve problems such as unnecessary hospital visits and neglect that may occur when the condition of the companion animal 11 is determined only by visual images.

Further, the management server 20 may rapidly and accurately manage the companion animal 11 by providing the recommendation information to the user terminal 10 according to the current condition or disease condition of the companion animal 11.

Such a management server 20 may be implemented by hardware circuits (e.g., complementary metal-oxide-semiconductor (CMOS)-based logic circuits), firmware, software, or a combination thereof. For example, the management server 20 may be implemented using transistors, logic gates, and electronic circuits in the form of various electrical structures.

The service-linked terminal 30 is a terminal of one of a plurality of veterinary hospitals that manage and treat the health of the companion animal 11, and may perform the treatment of the companion animal 11 more rapidly using the result data.

The service-linked terminal 30 may share the hospital record information with the user terminal 10, the management server 20, and a separate server.

The service-linked terminal 30 may provide the hospital information and the notification information to the user terminal 10 and/or the management server 20.

In some embodiments, the service-linked terminal 30 may include separate facilities such as an abandoned dog center, an abandoned cat center, a shelter, and the like.

The manager terminal 40 is a terminal possessed by a separate manager, and may transmit or receive data in synchronization with the user terminal 10, the management server 20, and the service-linked terminal 30 in real time using a wireless communication network. In this case, the manager terminal 40 may transmit or receive data using an application program (or application).

The manager terminal 40 may learn the standard data received from the management server 20, analyze the photographed image data received from the user terminal 10, and generate the result data corresponding to the photographed image data.

In some embodiments, when the manager terminal 40 receives the photographed image data from the user terminal 10, the manager terminal 40 may compare and analyze the photographed image data on the basis of the standard data to generate the result data.

In some embodiments, when the result data is generated in the user terminal 10, the manager terminal 40 may receive the result data from the user terminal 10 and transmit the result data to the management server 20. Further, when the result data is generated in the management server 20, the manager terminal 40 may receive the result data from the management server 20 and transmit the result data to the user terminal 10.

In some embodiments, the manager terminal 40 may transmit or receive the medical treatment management data corresponding to the current condition or disease condition of the companion animal 11 on the basis of the result data to or from at least one of the user terminal 10, the management server 20, and the service-linked terminal 30.

Such a manager terminal 40 may include various portable electronic communication devices that support communication with the user terminal 10, the management server 20, and the service-linked terminal 30. For example, as a separate smart device, the manager terminal 40 may include one of various terminals such as smartphones, PDAs, tablet computers, wearable devices (e.g., watch type terminals (smartwatches), glasses type terminal (smart glasses), HMDs, etc.), and various types of IoT terminals, but the present invention is not limited thereto.

Figure 3:
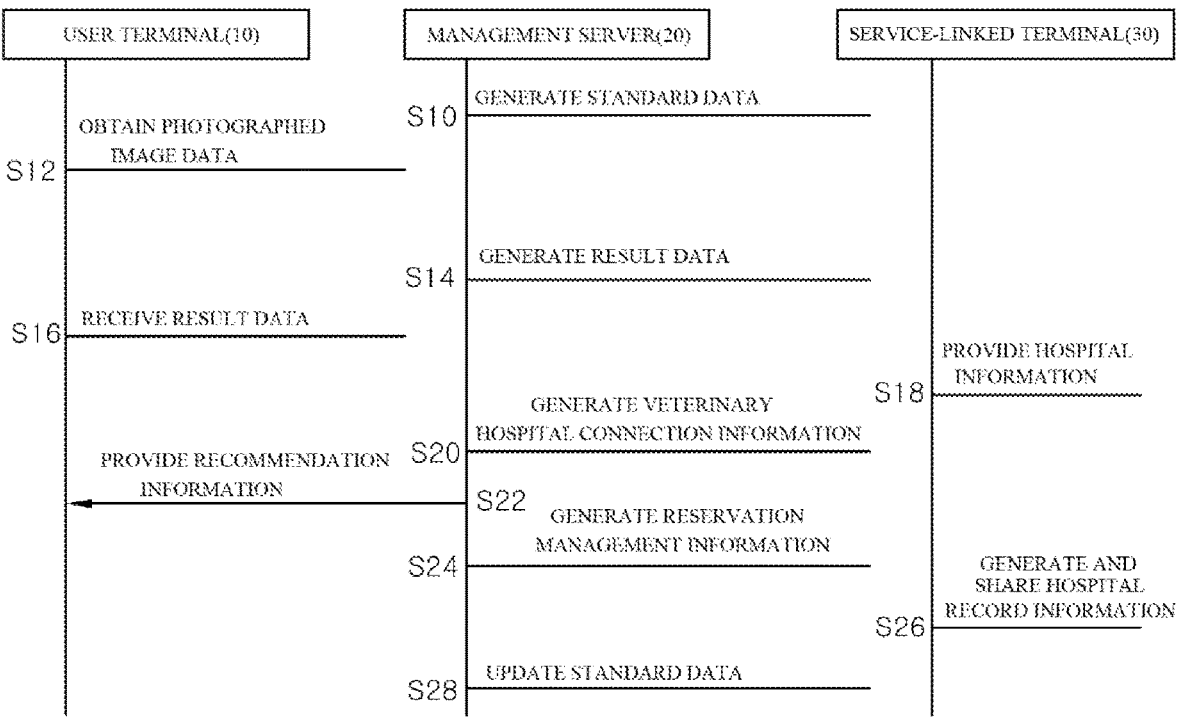
FIG. 3 is a diagram for describing a service providing method for predicting and diagnosing a joint condition according to an embodiment of the present invention.
Figure 7:
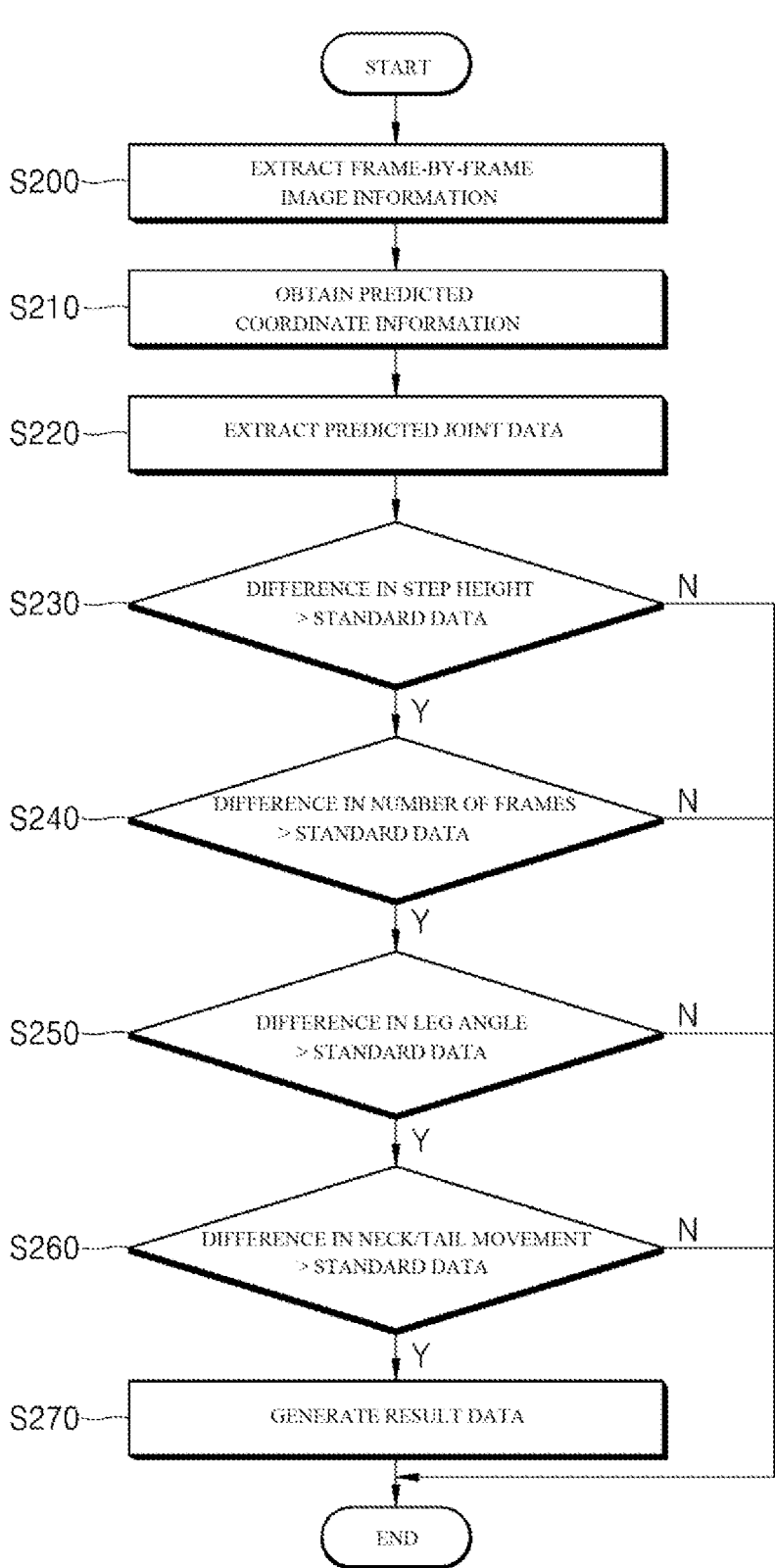
FIG. 7 is a diagram for describing an operation of generating result data illustrated in FIG. 3.
Figure 8:
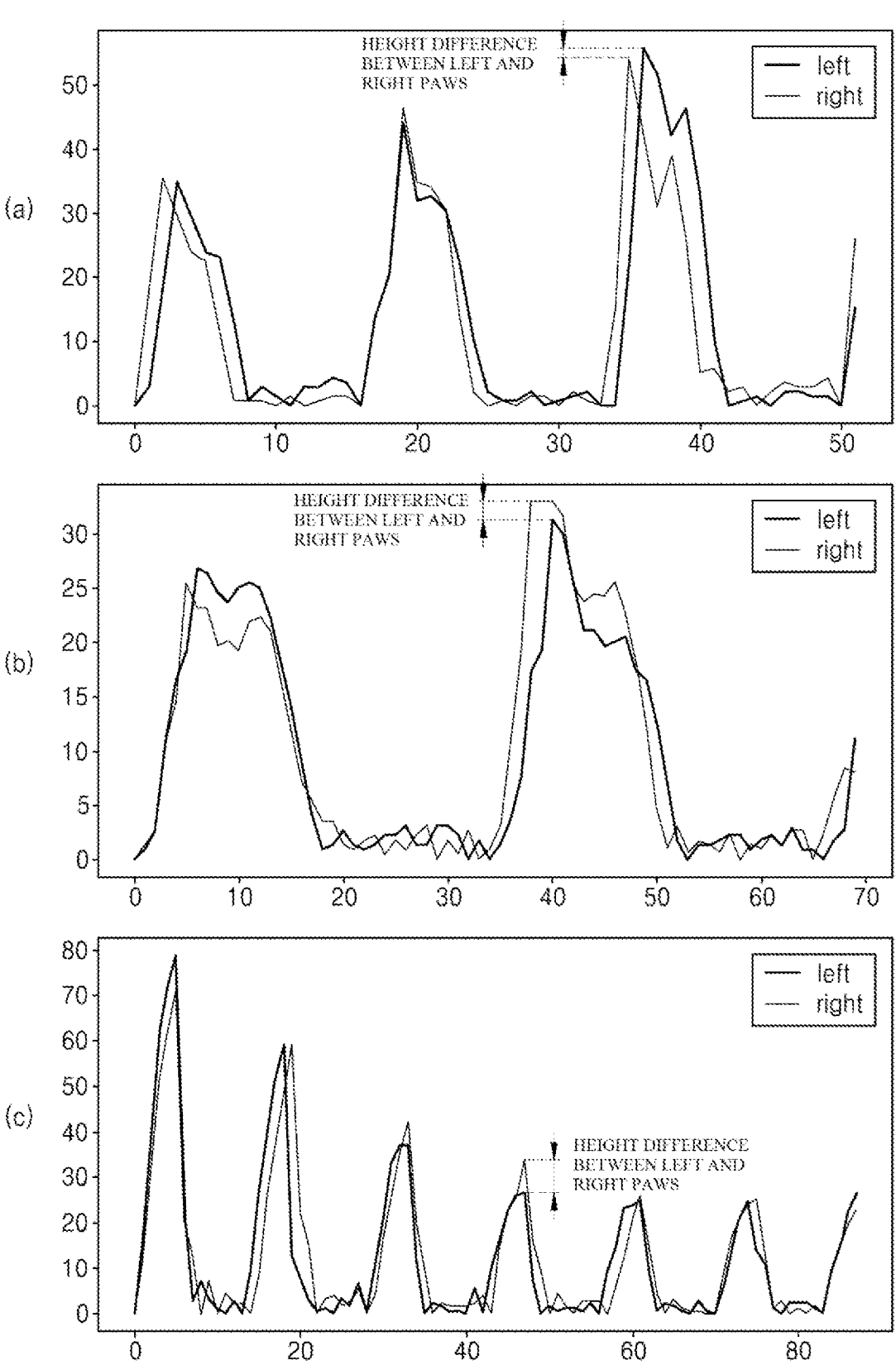
FIG. 8 is a set of diagrams for describing a normal step height difference illustrated in FIG. 7.
Figure 9:
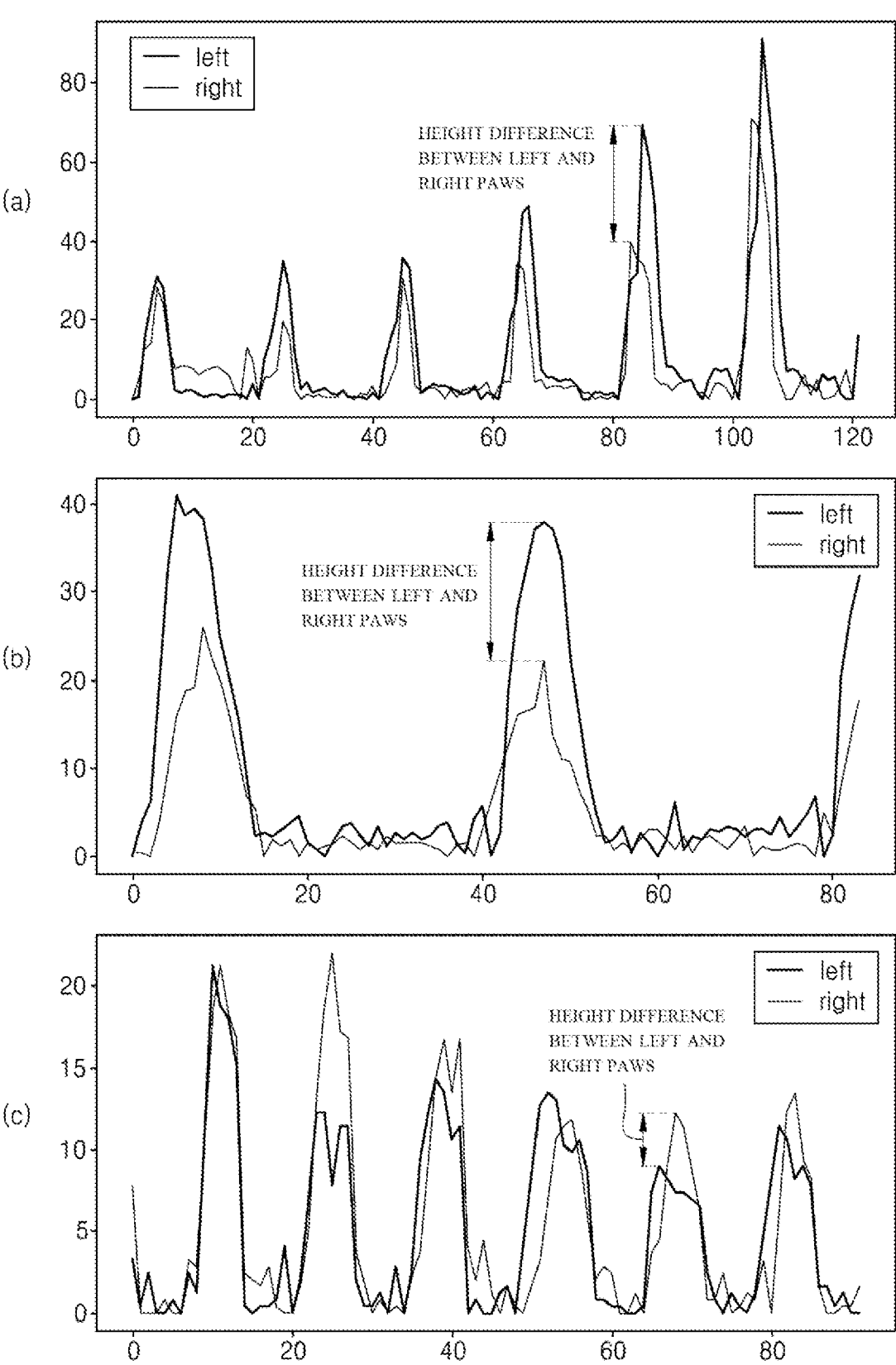
FIG. 9 is a set of diagrams for describing an abnormal step height difference illustrated in FIG. 7.
Figure 10:
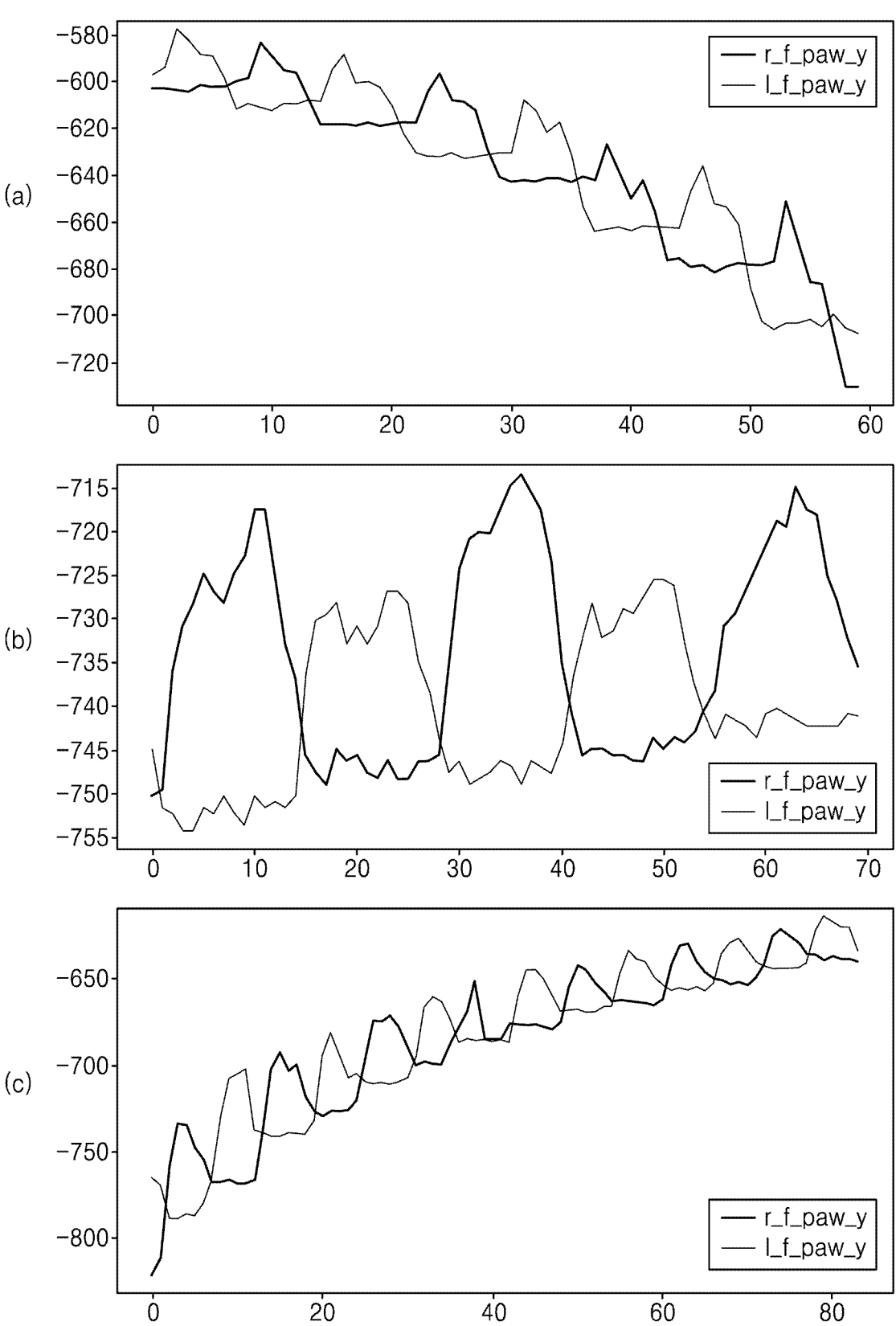
FIG. 10 is a set of diagrams for describing the number of normal frames illustrated in FIG. 7.
Figure 11:
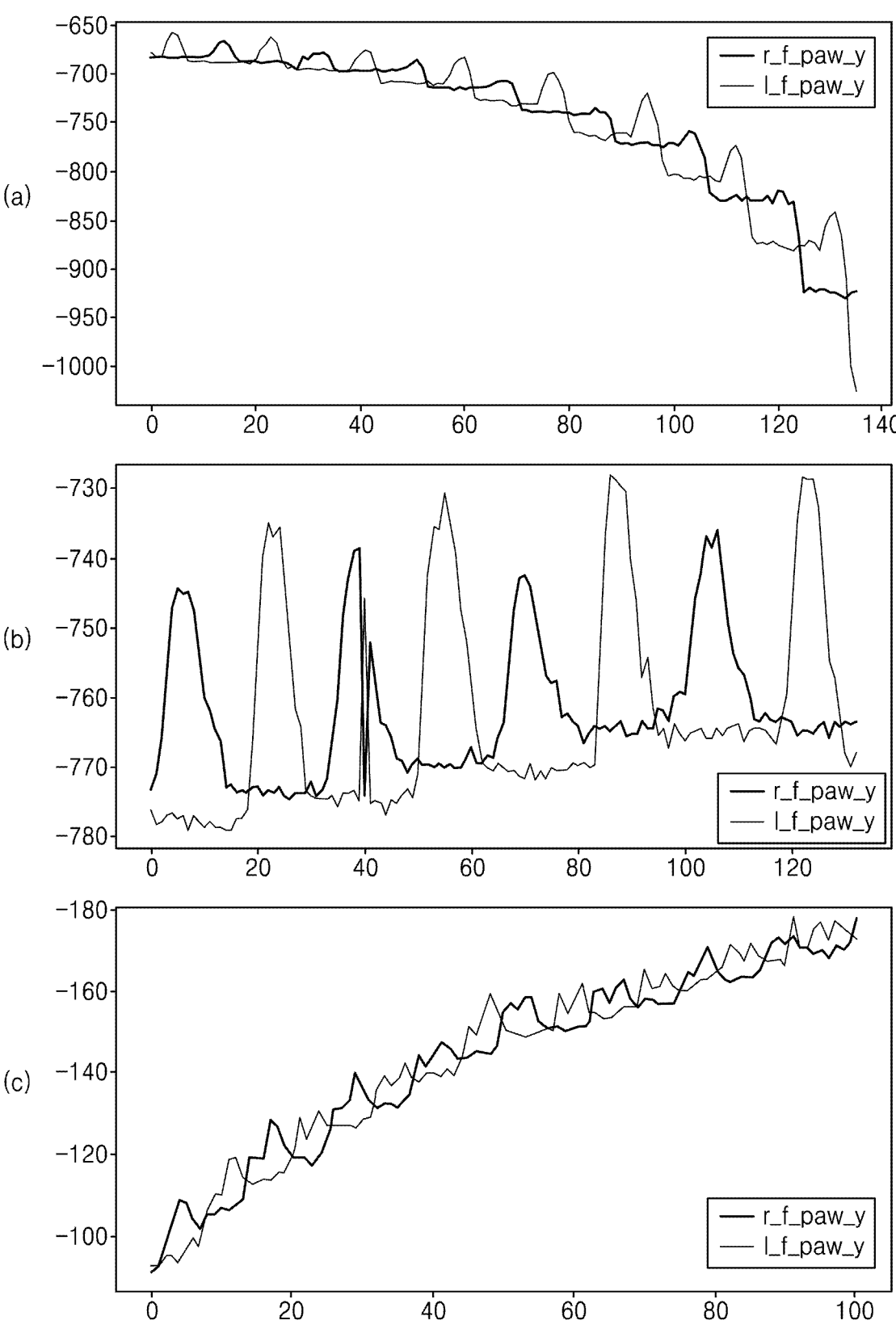
FIG. 11 is a set of diagrams for describing the number of abnormal frames illustrated in FIG. 7.
Figure 14:
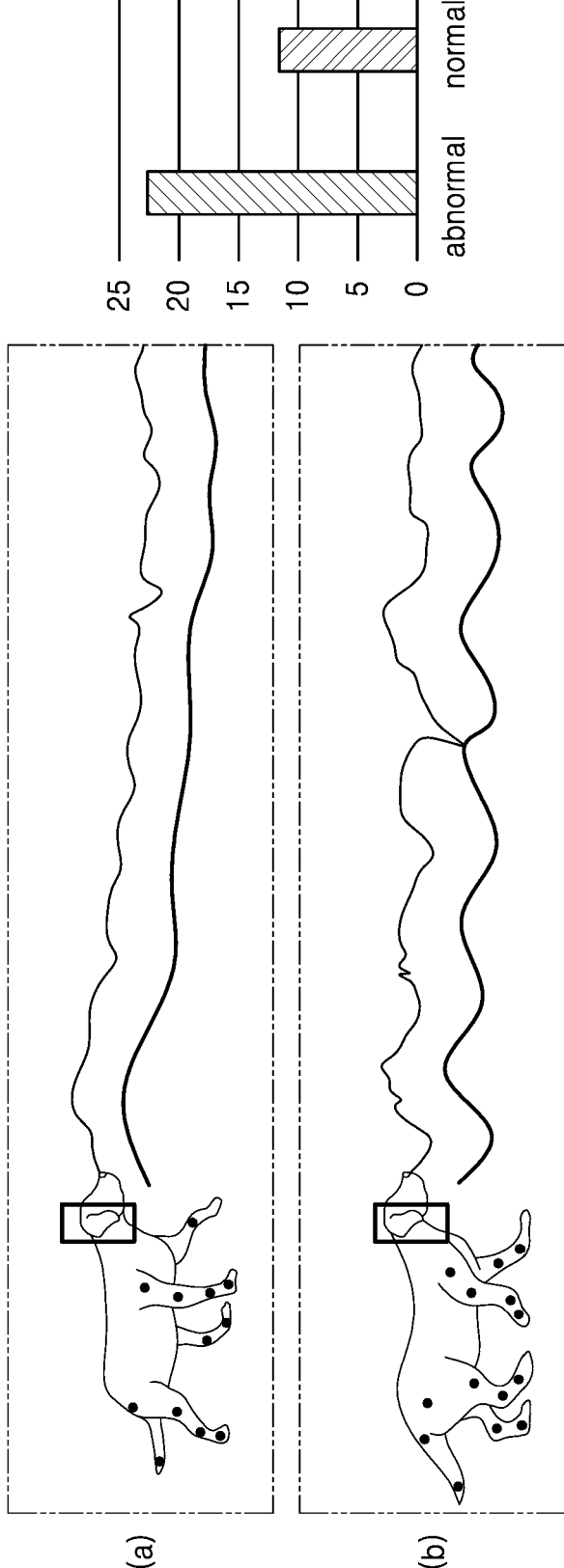
FIG. 14 is a set of diagrams for describing normal and abnormal conditions of movements of a neck and a tail through coordinate information of a forepaw illustrated in FIG. 7.
Figure 15:
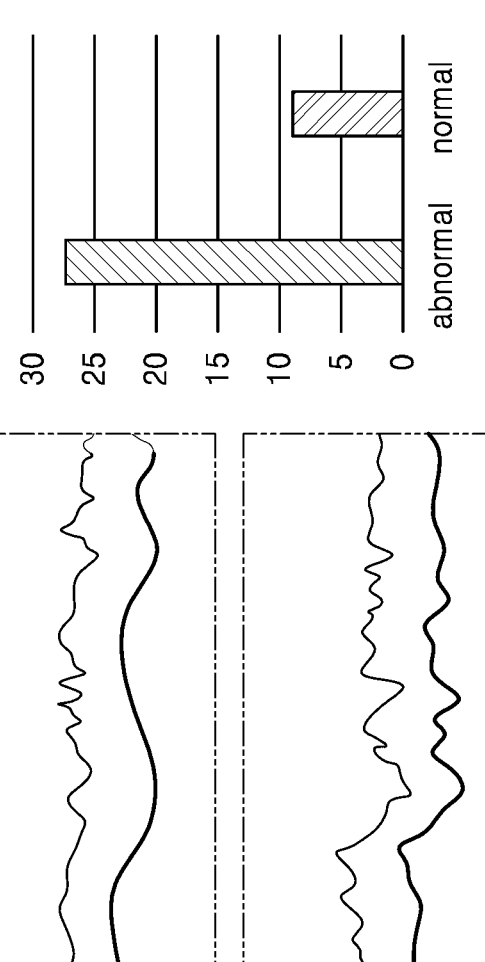
FIG. 15 is a set of diagrams for describing normal and abnormal conditions of movements of a neck and a tail through coordinate information of a hindpaw illustrated in FIG. 7.
Figure 16:
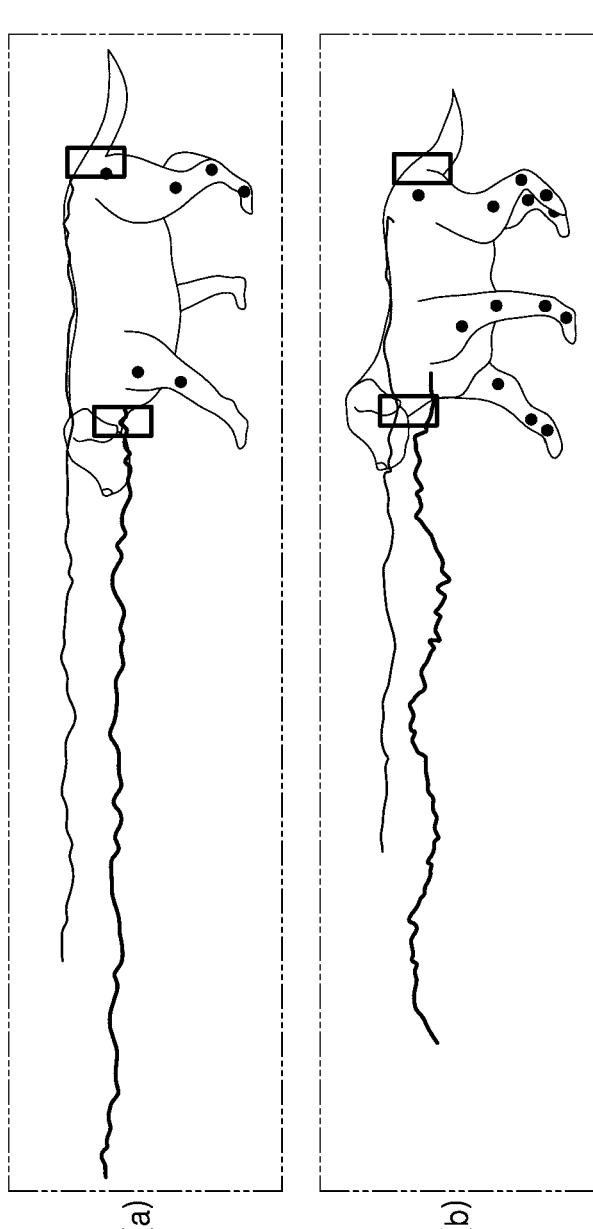
FIG. 16 is a set of diagrams for describing normal and abnormal conditions of movements of a neck and a tail through coordinate information of a forepaw and a hindpaw illustrated in FIG. 7.

The operation of the service providing system for predicting and diagnosing the joint condition according to the embodiment of the present invention having such a structure is as follows. FIG. 3 is a diagram for describing a service providing method for predicting and diagnosing a joint condition according to an embodiment of the present invention, FIG. 4 is a diagram for describing an operation of generating standard data illustrated in FIG. 3, FIG. 5 is a diagram for describing basic photographed information illustrated in FIG. 4, FIG. 6 is a set of diagrams for describing an operation of extracting and labeling standard coordinate information illustrated in FIG. 4, FIG. 7 is a diagram for describing an operation of generating result data illustrated in FIG. 3, FIG. 8 is a set of diagrams for describing a normal step height difference illustrated in FIG. 7, FIG. 9 is a set of diagrams for describing an abnormal step height difference illustrated in FIG. 7, FIG. 10 is a set of diagrams for describing the number of normal frames illustrated in FIG. 7, FIG. 11 is a set of diagrams for describing the number of abnormal frames illustrated in FIG. 7, FIG. 12 is a set of diagrams for describing an angle of a normal leg illustrated in FIG. 7, FIG. 13 is a set of diagrams for describing an angle of an abnormal leg illustrated in FIG. 7, FIG. 14 is a set of diagrams for describing normal and abnormal conditions of movements of a neck and a tail through coordinate information of a forepaw illustrated in FIG. 7, FIG. 15 is a set of diagrams for describing normal and abnormal conditions of movements of a neck and a tail through coordinate information of a hindpaw illustrated in FIG. 7, and FIG. 16 is a set of diagrams for describing normal and abnormal conditions of movements of a neck and a tail through coordinate information of a forepaw and a hindpaw illustrated in FIG. 7.

First, in the embodiment of the present invention, a companion animal 11 is disclosed as being limited to a puppy, but the present invention is not limited thereto.

As illustrated in FIG. 3, a management server 20 may generate standard data (S10).

Specifically, the management server 20 may obtain basic information from a plurality of companion animals 11 as illustrated in FIG. 4 (S100). Here, the basic information may include guardian information, abandonment information, hospital record information, unique identification number, dog breed or cat breed, sex, age, weight, neutered status, etc., but the present invention is not limited thereto.

In some embodiments, the management server 20 may input the basic information of the companion animal 11 using a separate mobile terminal.

Next, the management server 20 may obtain basic photographed information obtained by photographing movement of the companion animal 11 on the basis of the basic information (S110).

In some embodiments, the management server 20 may obtain the basic photographed information of the companion animal 11 using a separate photographing tool or scanner.

Next, the management server 20 may set a bounding box by recognizing the companion animal 11 included in the basic photographed information as an object (S120).

Specifically, the companion animal 11 included in the basic photographed information is separated from a background and recognized as the object, and then a boundary area may be detected around the recognized object, and the bounding box may be set for each frame. That is, by excluding entities other than the companion animal 11 included in the basic photographed information, it is possible to more accurately determine the movement of the companion animal 11 by preventing false detections that may occur due to such entities.

For example, referring to FIG. 5, the management server 20 may set a bounding box A around the recognized object.

Next, the management server 20 may set a direction of movement of the object located in the bounding box A (S130).

For example, referring to FIG. 5, the management server 20 may set the direction of the movement of the object from left to right on the basis of a video file.

That is, by setting the movement of the object recognized in one direction, it is possible to more accurately determine a joint condition of the object.

Next, the management server 20 may extract and label standard coordinate information B for a body part of the object located in the bounding box A (S140).

For example, referring to FIG. 6, the management server 20 may extract and label the standard coordinate information B for the body part of the recognized object (see FIG. 6A), and may store the standard coordinate information B corresponding thereto in Extensible Markup Language (XML) format (see FIG. 6B).

In the present embodiment, the video file may be a video file in which the companion animal 11 walking in a consistent direction is recorded for 10 seconds or more.

In some embodiments, the management server 20 may extract the standard coordinate information B for the body part of the object for each frame (see FIG. 6C).

Next, the management server 20 may generate standard derivative information using the extracted standard coordinate information B (S150).

In this case, the extracted standard coordinate information B may be extracted as coordinates in XML format, converted into a file for input to a pose estimation model among a plurality of convolution layers of a CNN, and then preceded by an operation for coordinate outlier verification and a preprocessing operation for correction and standardization.

Specifically, the management server 20 may generate the standard derived variable for at least one variable among a step height between right and left paws of the object, a number of frames corresponding to a change in movement of the object, at least one leg angle of the object, and movements of a neck and tail of the object to generate the standard data.

Next, the standard parameter may be set based on the standard derived variable and then the standard joint data may be obtained by inputting the standard parameter into the pose estimation model, the standard result data corresponding to the obtained standard joint data may be generated (S160), and then the standard data may be generated by verifying the standard data generated by iteratively learning the standard result data (S170 and S180).

That is, the management server 20 may match the standard condition information and the standard result data, and generate the standard data by repeatedly learning based on a CNN algorithm, and thus verify suitability.

Next, when the guardian requests a diagnosis of the current condition or disease condition of the companion animal 11, the user terminal 10 may obtain the photographed image data for the movement of the companion animal 11 (S12).

In some embodiments, the photographed image data for the movement of the companion animal 11 may be obtained through a separate photographing device.

In this case, the photographed image data may be a video file in which the companion animal 11, which is a subject for which a joint condition is predicted and diagnosed, walking in a consistent direction is recorded for 10 seconds or longer.

Next, the management server 20 may generate result data corresponding to the photographed image data on the basis of the standard data (S14).

Specifically, referring to FIG. 7, the management server 20 may pre-process the video included in the photographed image data and extract a corrected image for each frame (S200).

Specifically, the management server 20 may extract frame-by-frame image information for joint analysis from the video in which brightness, sharpness, etc. are automatically corrected, included in the photographed image data.

Next, the management server 20 may obtain predicted coordinate information of the companion animal 11 using the frame-by-frame image information (S210).

Specifically, the management server 20 may separate the companion animal 11 included in the frame-by-frame image information from a background to recognize the companion animal 11 as an object, then detect a boundary area around the recognized object to set a bounding box for each frame, and extract frame-by-frame predicted coordinate information about the body part of the object located in the set bounding box.

In some embodiments, the management server 20 may label the predicted coordinate information on the basis of an object movement direction.

In the present embodiment, examples of the body part may include a body part of the companion animal 11, such as a leg, a neck, a tail, etc., but the present invention is not limited thereto.

Next, the management server 20 may generate a derived variable using the extracted predicted coordinate information, and extract the predicted joint data by inputting the generated derived variable to the pose estimation model (S220).

Specifically, the management server 20 may generate the derived variable for at least one variable among a step height between right and left paws of the object, a number of frames corresponding to a change in movement of the object, at least one leg angle of the object, and movements of a neck and tail of the object to extract the predicted joint data.

Specifically, the management server 20 may analyze a difference in step height between the right and left paws of the object, and when the difference in step height is greater than or equal to a set average value on the basis of the standard data (S230), the management server 20 may generate the result data indicating that it is determined that there is an abnormality in the joint of the companion animal 11 (S270).

For example, as illustrated in FIG. 8, in the case of photographing a front of the companion animal 11 (see FIG.

8A), in the case of photographing a side of the companion animal 11 (see FIG. 8B), or in the case of photographing a back of the companion animal 11 (see FIG. 8C), when a difference in height between the left and right paws is found to be small through the predicted coordinate information corresponding thereto, it is determined that the companion animal 11 is in a normal condition, and result data indicating that it is determined that there is no abnormality in the joint of the companion animal 11 may be generated.

Unlike the above case, as illustrated in FIG. 9, in the case of photographing the front of the companion animal 11 (see FIG. 9A), in the case of photographing the side of the companion animal 11 (see FIG. 9B), or in the case of photographing the back of the companion animal 11 (see FIG. 9C), when a difference in height between the left and right paws is found to be large through the predicted coordinate information corresponding thereto, it is determined that the companion animal 11 is in an abnormal condition, and result data indicating that it is determined that there is an abnormality in the joint of the companion animal 11 may be generated.

Next, the management server 20 may analyze a difference in number of frames of steps of the object, and when the difference in number of frames is greater than or equal to a set average value on the basis of the standard data (S240), the management server 20 may generate result data indicating that it is determined that there is an abnormality in the joint of the companion animal 11 (S270).

For example, as illustrated in FIG. 10, in the case of photographing the front of the companion animal 11 (see FIG. 10A), in the case of photographing the side of the companion animal 11 (see FIG. 10B), or in the case of photographing the back of the companion animal 11 (see FIG. 10C), when a difference in number of frames is found to be small through the predicted coordinate information corresponding thereto, it is determined that the companion animal 11 is in a normal condition, and result data indicating that it is determined that there is no abnormality in the joint of the companion animal 11 may be generated.

Unlike the above case, as illustrated in FIG. 11, in the case of photographing the front of the companion animal 11 (see FIG. 11A), in the case of photographing the side of the companion animal 11 (see FIG. 11B), or in the case of photographing the back of the companion animal 11 (see FIG. 11C), when a difference in number of frames is found to be large through the predicted coordinate information corresponding thereto, it is determined that the companion animal 11 is in an abnormal condition, and result data indicating that it is determined that there is an abnormality in the joint of the companion animal 11 may be generated.

Next, the management server 20 may analyze a difference in leg angle corresponding to a change in movement of the object, and when the difference in leg angle is greater than or equal to a set average value on the basis of the standard data (S250), result data indicating that it is determined that there is an abnormality in the joint of the companion animal 11 may be generated (S270).

For example, as illustrated in FIG. 12, in the case of photographing the front of the left paw of the companion animal 11 (see FIG. 12A) or in the case of photographing the front of the right paw of the companion animal 11 (see FIG. 12B), when the difference in leg angle is found to be 1 to 3° on average through the predicted coordinate information corresponding thereto, it is determined that the companion animal 11 is in a normal condition, and result data indicating that it is determined that there is no abnormality in the joint of the companion animal 11 may be generated.

Unlike the above case, as illustrated in FIG. 13, in the case of photographing the front of the left paw of the companion animal 11 (see FIG. 13A) or in the case of photographing the front of the right paw of the companion animal 11 (see FIG. 13B), when the difference in leg angle is found to be 13 to 16° on average through the predicted coordinate information corresponding thereto, it is determined that the companion animal 11 is in an abnormal condition, and result data indicating that it is determined that there is an abnormality in the joint of the companion animal 11 may be generated.

Next, the management server 20 may analyze movements of the neck and tail of the object to analyze a difference in coordinate values corresponding to the change in movement, and when an MSE is greater than or equal to a set average value on the basis of the standard data (S260), result data indicating that it is determined that there is an abnormality in the joint of the companion animal 11 may be generated (S270).

For example, in the case of photographing the forepaw of the companion animal 11, when an MSE value is found to be 20 or more through the predicted coordinate information corresponding thereto, it is determined that the companion animal 11 is in an abnormal condition (see FIG. 14A), when the MSE value is found to be 15 or less through the predicted coordinate information corresponding thereto, it is determined that the companion animal 11 is in a normal condition (see FIG. 14B), and result data corresponding thereto may be generated.

Further, in the case of photographing the hindpaw of the companion animal 11, when the MSE value is 25 or more through the predicted coordinate information corresponding thereto, it is determined that the companion animal 11 is in an abnormal condition (see FIG. 15A), when the MSE value is 10 or less through the predicted coordinate information corresponding thereto, it is determined that the companion animal 11 is in a normal condition (see FIG. 15B), and result data corresponding thereto may be generated.

Further, in the case of photographing the forepaw and hindpaw of the companion animal 11, when the MSE value of the tail is found to be 6 or more and the MSE value of the neck is found to be 8 or more through the predicted coordinate information corresponding thereto, it is determined that the companion animal 11 is in an abnormal condition (see FIG. 16A), when the MSE value of the tail is found to be 4 or less and the MSE value of the neck is found to be 4 or less through the predicted coordinate information corresponding thereto, it is determined that the companion animal 11 is in a normal condition (see FIG. 16B), and result data corresponding thereto may be generated.

Next, the user terminal 10 may receive the result data corresponding to the photographed image data from the management server 20 (S16).

Next, the service-linked terminal 30 may provide hospital information on the basis of the standard data (S18).

Here, the provision of the hospital information may be previously performed, but the present invention is not limited thereto.

Next, the management server 20 may generate veterinary hospital connection information on the basis of the hospital information (S20).

Here, the generation of the veterinary hospital connection information may be previously performed, but the present invention is not limited thereto.

Next, the management server 20 may generate recommendation information corresponding to the result data on the basis of the veterinary hospital connection information to transmit the recommendation information to the user terminal 10 (S22).

Next, the management server 20 may generate reservation management information (S24).

For example, the management server 20 may receive a reservation request signal generated according to customized information from the user terminal 10, and receive reservation management information corresponding to the reservation request signal from the service-linked terminal 30 to transmit the reservation management information to the user terminal 10.

Next, the service-linked terminal 30 may generate and share hospital record information including treatment history information about the companion animal 11 (S26).

In this case, the hospital record information may be transmitted to the user terminal 10 and the management server 20.

Finally, the management server 20 may update the standard data in real time in response to the result data (S28).

The operations of the methods or algorithms in conjunction with the embodiments of the present invention may be implemented directly in hardware, implemented in a software module executed by hardware, or implemented by a combination thereof. The software module may reside in a random access memory (RAM), a read only memory (ROM), an erasable programmable ROM (EPROM), an electrically erasable programmable ROM (EEPROM), a flash memory, a hard disk, a removable disk, a compact disc read only memory (CD-ROM), or any form of computer-readable recording medium well known in the art.

Although embodiments of the present invention have been described with reference to the accompanying drawings, it will be understood by those skilled in the art to which the present invention pertains that various modifications can be made without departing from the scope of the present invention and without changing essential features. Therefore, the above-described embodiments should be considered in a descriptive sense only and not for purposes of limitation.

REFERENCE NUMERALS

1: SERVICE PROVIDING SYSTEM FOR PREDICTING AND DIAGNOSING JOINT CONDITION
11: COMPANION ANIMAL
10: USER TERMINAL
20: MANAGEMENT SERVER
30: SERVICE-LINKED TERMINAL
40: MANAGER TERMINAL

The invention claimed is:

1. A service providing method for predicting and diagnosing a joint condition, which is performed by a server, the service providing method comprising;

extracting frame-by-frame image information from photographed image data of a subject, wherein the photographed image data comprising: video inputting the frame-by-frame image information to a pose estimation model among a plurality of convolution layers of a convolution neural network (CNN) and extracting predicted joint data of the subject; and comparing and analyzing the predicted joint data extracted through the pose estimation model on the basis of standard data, determining whether there is an abnormality in a joint of the subject, and generating diagnosis result data, wherein the extracting of the predicted joint data includes separating the subject and a background from the frame-by-frame image information and recognizing the subject as an object, detecting a boundary area around the object and setting a bounding box for each frame, extracting frame-by-frame predicted coordinate information about a body part of the object located in the bounding box, extracting an object movement direction of the object located in the bounding box, and labeling the predicted coordinate information on the basis of the object movement direction and extracting the predicted joint data, wherein, in the generating of the result data, the movements of the neck and tail of the object are analyzed and a difference in coordinate values corresponding to a change in movement is analyzed, and when a mean squared error (MSE) is greater than or equal to a set average value on the basis of the standard data, result data indicating that it is determined that there is an abnormality in the joint of the subject is generated.

2. The service providing method of claim 1, wherein the extracting of the predicted joint data includes:

generating a derived variable using the predicted coordinate information; and inputting the derived variable to the pose estimation model on the basis of the standard data and extracting the predicted joint data.

3. The service providing method of claim 2, wherein, in the generating of the result data, the predicted coordinate information and standard coordinate information are matched for each frame on the basis of the standard data, and when a result of the matching is greater than or equal to a preset criterion, result data indicating that it is determined that there is an abnormality in the joint of the subject is generated.

4. The service providing method of claim 3, wherein the derived variable includes at least one of a step height between right and left paws of the object, a number of frames corresponding to a change in movement of the object, at least one leg angle of the object, and movements of a neck and tail of the object.

5. The service providing method of claim 4, wherein, in the generating of the result data, a difference in step height between the right and left paws of the object is analyzed, and when the difference in step height is greater than or equal to a set average value on the basis of the standard data, result data indicating that it is determined that there is an abnormality in the joint of the subject is generated.

6. The service providing method of claim 4, wherein, in the generating of the result data, a difference in number of frames corresponding to a change in movement of the object is analyzed, and when the difference in number of frames is greater than or equal to a set average value on the basis of the standard data, result data indicating that it is determined that there is an abnormality in the joint of the subject is generated.

7. The service providing method of claim 4, wherein, in the generating of the result data, at least one leg angle of the object is analyzed and a difference in leg angle corresponding to a change in movement is analyzed, and when the difference in leg angle is greater than or equal to a set average value on the basis of the standard data, result data indicating that it is determined that there is an abnormality in the joint of the subject is generated.

8. The service providing method of claim 1, further comprising generating the standard data, wherein the generating of the standard data includes:

extracting an image for each frame from a video;

extracting and labeling standard coordinate information about a body part of an object included in the extracted image;

generating a standard derived variable using the standard coordinate information;

setting a standard parameter on the basis of the standard derived variable and then inputting the set standard parameter to the pose estimation model; and iteratively learning standard joint data obtained through the pose estimation model and standard result data corresponding to the standard joint data and verifying the generated standard data.

9. The service providing method of claim 1, further comprising labeling the predicted joint data for each frame that is extracted through the pose estimation model for each subject.

10. The service providing method of claim 1, wherein the photographed image data is a video file in which the subject walking in a consistent direction is recorded for 10 seconds or longer.

11. A computer program which is stored in a non-transitory computer-readable recording medium to perform the method of claim 1 in combination with a computer that is hardware.

12. A service providing system for predicting and diagnosing a joint condition, comprising:

a user terminal configured to obtain photographed image data from a subject to be examined, wherein the photographed image data comprising: video, and a management server configured to extract frame-by-frame image information from the photographed image data of the subject, input the frame-by-frame image information to a pose estimation model among a plurality of convolution layers of a convolution neural network (CNN) to extract predicted joint data of the subject, compare and analyze the predicted joint data extracted through the pose estimation model on the basis of standard data, determine whether there is an abnormality in a joint of the subject, and generate diagnosis result data, wherein the management server separates the subject and a background from the frame-by-frame image information to recognize the subject as an object, detects a boundary area around the object to set a bounding box for each frame, extracts frame-by-frame predicted coordinate information about a body part of the object located in the bounding box, extracts an object movement direction of the object located in the bounding box, and labels the predicted coordinate information on the basis of the object movement direction to extract the predicted joint data, wherein, in the generating of the result data, the movements of the neck and tail of the object are analyzed and a difference in coordinate values corresponding to a change in movement is analyzed, and when a mean squared error (MSE) is greater than or equal to a set average value on the basis of the standard data, result data indicating that it is determined that there is an abnormality in the joint of the subject is generated.

13. The service providing system of claim 12, further comprising a service-linked terminal configured to share medical treatment management data generated in response to the result data.

14. The service providing system of claim 12, further comprising a manager terminal configured to learn the standard data and generate the result data corresponding to the photographed image data.

\* \* \* \* \*